United States Patent [19]
Cruse et al.

[11] Patent Number: 6,127,468
[45] Date of Patent: Oct. 3, 2000

[54] FILLED RUBBERS COMPRISING BLOCKED MERCAPTOSILANES AND THIURAM DEBLOCKING AGENTS

[75] Inventors: Richard W. Cruse, Yorktown Heights; Robert J. Pickwell, Tonawanda, both of N.Y.

[73] Assignee: CK Witco Corporation, Del.

[21] Appl. No.: 09/252,559

[22] Filed: Feb. 19, 1999

Related U.S. Application Data

[63] Continuation-in-part of application No. PCT/US98/17391, Aug. 21, 1998.
[60] Provisional application No. 60/056,566, Aug. 21, 1997, abandoned.

[51] Int. Cl.[7] .............................. C08K 5/40; C08K 5/549; C08K 5/5419; C08K 5/36; C08K 3/00
[52] U.S. Cl. ........................ 524/225; 524/262; 524/265; 524/269; 524/280; 524/282; 524/283; 524/392
[58] Field of Search ..................................... 524/225, 262, 524/265, 269, 280, 282, 283, 392

[56] References Cited

U.S. PATENT DOCUMENTS

| | | |
|---|---|---|
| 3,502,704 | 3/1970 | McKeller et al. . |
| 3,692,812 | 9/1972 | Berger . |
| 3,922,436 | 11/1975 | Bell et al. . |
| 3,957,718 | 5/1976 | Pochert et al. . |
| 4,060,539 | 11/1977 | Seiler et al. ............... 260/448.8 R |
| 4,184,998 | 1/1980 | Shippy et al. . |
| 4,519,430 | 5/1985 | Ahmad et al. . |
| 4,820,751 | 4/1989 | Takeshita et al. . |

FOREIGN PATENT DOCUMENTS

| | | | |
|---|---|---|---|
| 10082/97 | 7/1997 | Australia | ......................... C08K 5/54 |
| 1008297 | 7/1997 | Australia . | |
| 2508931 | 9/1976 | Germany . | |
| 9817391 | 8/1998 | WIPO . | |

OTHER PUBLICATIONS

Meeting Minutes, "Improved Performance of Silica and Carbon Black Filled Elastomers"—Dec. 17, 1998.
Preparation of Silylalkanethiols—XP–002084433—Jan. 1968.
Trialkoxysilylalkanethiols and Bis (trialkoxysilylakyl) sulfides—XP–002084434—Aug. 1977.
Epoxy Resins Potting Compositions for Semiconductor Devices XP–002084435—Sep. 4, 1989.
Derwent Abstract—Japanese Patent No. 63270751 Nov. 8, 1988.

*Primary Examiner*—David W. Wu
*Assistant Examiner*—Kelechi C. Egwim
*Attorney, Agent, or Firm*—Raymond D. Thompson

[57] ABSTRACT

This invention describes the use of novel blocked mercaptosilanes, wherein the hydrogen atom of the mercaptan functionality has been substituted, in filled polymers. The blocked mercaptosilanes described are unique in that they allow the mixing of fillers with organic polymers to proceed while remaining inert toward coupling to the polymer. The coupling reactions of these blocked mercaptosilicon compounds are triggered by addition of an appropriate deblocking agent, which preferably is tetramethylthiuram monosulfide.

5 Claims, No Drawings

FILLED RUBBERS COMPRISING BLOCKED MERCAPTOSILANES AND THIURAM DEBLOCKING AGENTS

This application is a continuation-in-part of international application PCT/US98/17391, designating the United States, filed Aug. 21, 1998, which claims priority to U.S. provisional patent application Ser. No. 06/056,566, filed Aug. 21, 1997, now abandoned.

FIELD OF THE INVENTION

This invention relates to the use of sulfur silane coupling agents which are latent, that is, they are in a state of reduced activity until such a time as one finds it useful to activate them. The invention also relates to the manufacture of rubbers including inorganic fillers and these silane coupling agents, as well as to the manufacture of the silanes.

BACKGROUND

The majority of prior art in the use of sulfur-containing coupling agents in rubber involves silanes containing one or more of the following chemical bonds types: S—H (mercapto), S—S (disulfide or polysulfide), or C=S (thiocarbonyl). Mercaptosilanes have offered superior coupling at substantially reduced loadings; however, their high chemical reactivity leads to unacceptably high viscosities during processing and premature curing (scorch). Their undesirability is aggravated by their odor. As a result, other, less reactive coupling agents have been found. Hence, a compromise must be found between coupling and the associated final properties, processability, and required loading levels, which invariably leads to the need to use substantially higher coupling agent loadings than would be required with mercaptosilanes, and often also to the need to deal with less than optimal processing conditions, both of which lead to higher costs.

The prior art discloses acylthioalkyl silanes, such as $CH_3C(=O)S(CH_2)_{1-3}Si(OR)_3$ [M. G. Voronkov et al. in *Inst. Org. Khim.*, Irkutsk, Russia] and $HOC(=O)CH_2CH_2C(=O)S(CH_2)_3Si(OC_2H_5)_3$ [U.S. Pat. No. 3,922,436 to R. Bell et al.]. Takeshita and Sugawara disclosed in Japanese Patent JP 63270751A2 the use of compounds represented by the general formula, $CH_2=C(CH_3)C(=O)S(CH_2)_{1-6}Si(OCH_3)_3$ in tire tread compositions, but these compounds are not desirable because the unsaturation $\alpha,\beta$ to the carbonyl group of the thioester has the undesirable potential to polymerize during the compounding process or during storage.

Prior art by Yves Bomal and Olivier Durel, in Australian Patent AU-A-10082/97, discloses the use in rubber of silanes of the structure represented by $R^1{}_nX_{3-n}Si—(Alk)_m(Ar)_p—S(C=O)—R$ where $R^1$ is phenyl or alkyl; X is halogen, alkoxy, cycloalkoxy, acyloxy, or OH; Alk is alkyl; Ar is aryl; R is alkyl, alkenyl, or aryl; n is 0 to 2; and m and p are each 0 or 1, but not both zero. This prior art, however, stipulates that compositions of these silanes must be used in conjunction with functionalized siloxanes. In addition, the prior art does not disclose nor suggest the use of these silanes as latent mercaptosilane coupling agents, nor does it disclose nor suggest the use of these compounds in any way which would give rise to the advantages of using them as a source of latent mercaptosilane.

U.S. Pat. No. 4,519,430 to Ahamd et al. and U.S. Pat. No. 4,184,998 to Shippy et al. disclose the blocking of a mercaptosilane with an isocyanate to form a solid which is added to a tire composition, which mercaptan reacts into the tire during heating, which could happen at any time during processing since this a thermal mechanism. The purpose of this silane is to avoid the sulfur smell of the mercaptosilane, not to improve the processing of the tire. Moreover, the isocyanate used has toxicity issues, when used to make the silane and when released during rubber processing.

U.S. Pat. No. 3,957,718 to Porchet et al. discloses compositions containing silica, phenoplasts or aminoplasts and silanes such as xanthates, thioxanthates and dithiocarbamates; however, the prior art does not disclose nor suggest the use of these silanes as latent mercaptosilane coupling agents nor as the advantage of using them as a source of latent mercaptosilane. There remains a need for effective latent coupling agents which exhibit the advantages of mercaptosilanes without exhibiting the disadvantages such as described herein.

SUMMARY OF THE INVENTION

The silanes of the present invention are mercaptosilane derivatives in which the mercapto group is blocked ("blocked mercaptosilanes"), i.e., the mercapto hydrogen atom is replaced by another group (hereafter referred to as "blocking group"). Specifically, the silanes of the present invention are blocked mercaptosilanes in which the blocking group contains an unsaturated heteroatom or carbon chemically bound directly to sulfur via a single bond. This blocking group optionally may be substituted with one or more carboxylate ester or carboxylic acid functional groups. The use of these silanes in the manufacture of inorganic filled rubbers is taught wherein they are deblocked by the use of a deblocking agent during the manufacturing process.

DETAILED DESCRIPTION OF THE INVENTION

Silane Structures

The blocked mercptosilanes can be represented by the Formulae (1–2):

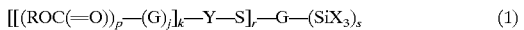  (1)

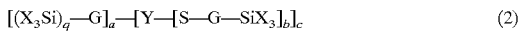  (2)

wherein

Y is a polyvalent species $(Q)_zA(=E)$, preferably selected from the group consisting of —C(=NR)—; —SC(=NR)—; —SC(=O)—; (—NR)C(=O)—; (—NR)C(=S)—;—OC(=O)—; —OC(=S)—; —C(=O)—; —SC(=S)—; —C(=S)—; —S(=O)—; —S(=O)$_2$—; —OS(=O)$_2$—; (—NR)S(=O)$_2$—; —SS(=O)—; —OS(=O)—; (—NR)S(=O)—; —SS(=O)$_2$—; (—S)$_2$P(=O)—; —(—S)P(=O)—; —P(=O)(-)$_2$; (—S)$_2$P(=S)—; —(—S)P(=S)—; —P(=S)(-)$_2$; (—NR)$_2$P(=O)—; (—NR)(—S)P(=O)—; (—O)(—NR)P(=O)—; (—O)(—S)P(=O)—; (—O)$_2$P(=O)—; —(—O)P(=O)—; —(—NR)P(=O)—; (—NR)$_2$P(=S)—; (—NR)(—S)P(=S)—; (—O)(—NR)P(=S)—; (—O)(—S)P(=S)—; (—O)$_2$P(=S)—; —(—O)P(=S)—; and —(—NR)P(=S)—; each wherein the atom (A) attached to the unsaturated heteroatom (E) is attached to the sulfur, which in turn is linked via a group G to the silicon atom;

each R is chosen independently from hydrogen, straight, cyclic or branched alkyl that may or may not contain unsaturation, alkenyl groups, aryl groups, and aralkyl groups, with each R containing from 1 to 18 carbon atoms;

each G is independently a monovalent or polyvalent group derived by substitution of alkyl, alkenyl, aryl or aralkyl wherein G can contain from 1 to 18 carbon atoms, with the proviso that G is not such that the silane would contain an α,β-unsaturated carbonyl including a carbon—carbon double bond next to the thiocarbonyl group, and if G is univalent (i.e., if p=0), G can be a hydrogen atom;

X is independently a group selected from the group consisting of —Cl, —Br, RO—, RC(=O)O—, R$_2$C=NO—, R$_2$NO— or R$_2$N—, —R, —(OSiR$_2$), (OSiR$_3$) wherein each R and G is as above and at least one X is not —R;

Q is oxygen, sulfur or (—NR—);

A is carbon, sulfur, phosphorus, or sulfonyl;

E is oxygen, sulfur or NR;

p is 0 to 5; r is 1 to 3; z is 0 to 2; q is 0 to 6; a is 0 to 7; b is 1 to 3; j is 0 to 1, but it maybe only if p is 1, c is 1 to 6, preferably 1 to 4; t is to 5; s is 1 to 3; k is 1 to 2, with the provisos that (A) if A is carbon, sulfur or sulfonyl, then (i) a+b=2 and (ii) k=1; (B) if A is phosphorus, then a+b=3 unless both (i) c>1 and (ii) b=1, in which case a=c+1; and (C) if A is phosphorus, then k is 2.

As used herein, "alkyl" includes straight, branched and cyclic alkyl groups, and "alkenyl" includes straight, branched and cyclic alkenyl groups containing one or more carbon—carbon double bonds. Specific alkyls include methyl, ethyl, propyl, isobutyl, and specific aralkyls include phenyl, tolyl and phenethyl. As used herein, "cyclic alkyl" or "cyclic alkenyl" also includes bicyclic and higher cyclic structures, as well as cyclic structures further substituted with alkyl groups. Representive examples include norbornyl, norbornenyl, ethylnorbornyl, ethylnorbornenyl, ethylcyclohexyl, ethylcyclohexenyl, and cyclohexylcyclohexyl.

Preferred silanes would be one wherein Y is RC(=O)— wherein R has a primary carbon attached to the carbonyl and is a C$_2$–C$_{12}$ alkyl, more preferably a C$_6$–C$_8$ alkyl; and X$_3$SiGSC(=O)GC(=O)SGSiX$_3$ wherein G is a divalent hydrocarbon.

Examples of G include —(CH$_2$)$_n$— wherein n is 1 to 12, diethylene cyclohexane, 1,2,4-triethylene cyclohexane, and diethylene benzene. It is preferred that the sum of the carbon atoms within the G groups within the molecule are from 3 to 18, more preferably 6 to 14. This amount of carbon in the blocked mercaptosilane facilitates the dispersion of the inorganic filler into the organic polymers, thereby improving the balance of properties in the cured filled rubber.

Preferable R groups are alkyls of C$_1$ to C$_4$ and H.

Specific examples of X are methoxy, ethoxy, isobutoxy, propoxy, isopropoxy, acetoxy and oximato. Methoxy, acetoxy and ethoxy are preferred. At least one X must be reactive (i.e., hydrolyzable).

Preferred embodiments are wherein p is 0 to 2; X is RO— or RC(=O)O—; R are hydrogen, phenyl, isopropyl, cyclohexyl, or isobutyl; G is a substituted phenyl or substituted straight chain alkyl of C$_2$ to C$_{12}$. The most preferred embodiments include those wherein p is zero; X is ethoxy and G is a C$_3$–C$_{12}$ alkyl derivative.

Representative examples of the silanes include 2-triethoxysilyl-1-ethyl thioacetate; 2-trimethoxysilyl-1-ethyl thioacetate; 2-(methyldimethoxysilyl)-1-ethyl thioacetate; 3-trimethoxysilyl-1-propyl thioacetate; triethoxysilylmethyl thioacetate; trimethoxysilylmethyl thioacetate; triisopropoxysilylmethyl thioacetate; methyldiethoxysilylmethyl thioacetate; methyldimethoxysilylmethyl thioacetate; methyldiisopropoxysilylmethyl thioacetate; dimethylethoxysilylmethyl thioacetate; dimethylmethoxysilylmethyl thioacetate; dimethylisopropoxysilylmethyl thioacetate; 2-triisopropoxysilyl-1-ethyl thioacetate; 2-(methyldiethoxysilyl)-1-ethyl thioacetate; 2-(methyldiisopropoxysilyl)-1-ethyl thioacetate; 2-(dimethylethoxysilyl)-1-ethyl thioacetate; 2-(dimethylmethoxysilyl)-1-ethyl thioacetate; 2-(dimethylisopropoxysilyl)-1-ethyl thioacetate; 3-triethoxysilyl-1-propyl thioacetate; 3-triisopropoxysilyl-1-propyl thioacetate; 3-methyldiethoxysilyl-1-propyl thioacetate; 3-methyldimethoxysilyl-1-propyl thioacetate; 3-methyldiisopropoxysilyl-1-propyl thioacetate; 1-(2-triethoxysilyl-1-ethyl)-4-thioacetylcyclohexane; 1-(2-triethoxysilyl-1-ethyl)-3-thioacetylcyclohexane; 2-triethoxysilyl-5-thioacetylnorbornene; 2-triethoxysilyl-4-thioacetylnorbornene; 2-(2-triethoxysilyl-1-ethyl)-5-thioacetylnorbornene; 2-(2-triethoxysilyl-1-ethyl)-4-thioacetylnorbornene; 1-(1-oxo-2-thia-5-triethoxysilylpenyl)benzoic acid; 6-triethoxysilyl-1-hexyl thioacetate; 1-triethoxysilyl-5-hexyl thioacetate; 8-triethoxysilyl-1-octyl thioacetate; 1-triethoxysilyl-7-octyl thioacetate; 6-triethoxysilyl-1-hexyl thioacetate; 1-triethoxysilyl-5-octyl thioacetate; 8-trimethoxysilyl-1-octyl thioacetate; 1-trimethoxysilyl-7-octyl thioacetate; 10-triethoxysilyl-1-decyl thioacetate; 1-triethoxysilyl-9-decyl thioacetate; 1-triethoxysilyl-2-butyl thioacetate; 1-triethoxysilyl-3-butyl thioacetate; 1-triethoxysilyl-3-methyl-2-butyl thioacetate; 1-triethoxysilyl-3-methyl-3-butyl thioacetate; 3-trimethoxysilyl-1-propyl thiooctoate; 3-triethoxysilyl-1-propyl thiopalmitate; 3-triethoxysilyl-1-propyl thiooctoate; 3-triethoxysilyl-1-propyl thiobenzoate; 3-triethoxysilyl-1-propyl thio-2-ethylhexanoate; 3-methyldiacetoxysilyl-1-propyl thioacetate; 3-triacetoxysilyl-1-propyl thioacetate; 2-methyldiacetoxysilyl-1-ethyl thioacetate; 2-triacetoxysilyl-1-ethyl thioacetate; 1-methyldiacetoxysilyl-1-ethyl thioacetate; 1-triacetoxysilyl-1-ethyl thioacetate; tris-(3-triethoxysilyl-1-propyl)trithiophosphate; bis-(3-triethoxysilyl-1-propyl) methyldithiophosphonate; bis-(3-triethoxysilyl-1-propyl) ethyldithiophosphonate; 3-triethoxysilyl-1-propyldimethylthiophosphinate; 3-triethoxysilyl-1-propyldiethylthiophosphinate; tris-(3-triethoxysilyl-1-propyl)tetrathiophosphate; bis-(3-triethoxysilyl-1-propyl) methyltrithiophosphonate; bis-(3-triethoxysilyl-1-propyl) ethyltrithiophosphonate; 3-triethoxysilyl-1-propyldimethyldithiophosphinate; 3-triethoxysilyl-1-propyldiethyldithiophosphinate; tris-(3-methyldimethoxysilyl-1-propyl)trithiophosphate; bis-(3-methyldimethoxysilyl-1-propyl)methyldithiophosphonate; bis-(3-methyldimethoxysilyl-1-propyl) ethyldithiophosphonate; 3-methyldimethoxysilyl-1-propyldimethylthiophosphinate; 3-methyldimethoxysilyl-1-propyldiethylthiophosphinate; 3-triethoxysilyl-1-propylmethylthiosulphate; 3-triethoxysilyl-1-propylmethanethiosulphonate; 3-triethoxysilyl-1-propylethanethiosulphonate; 3-triethoxysilyl-1-propylbenzenethiosulphonate; 3-triethoxysilyl-1-propyltoluenethiosulphonate; 3-triethoxysilyl-1-propylnaphthalenethiosulphonate; 3-triethoxysilyl-1-propylxylenethiosulphonate; triethoxysilylmethylmethylthiosulphate; triethoxysilylmethylmethanethiosulphonate; triethoxysilylmethylethanethiosulphonate; triethoxysilylmethylbenzenethiosulphonate; triethoxysilylmethyltoluenethiosulphonate; triethoxysilylmethylnaphthalenethiosulphonate; triethoxysilylmethylxylenethiosulphonate.

Mixtures of various blocked mercaptosilanes may be used, including those wherein synthetic methods result in a distribution of various silanes or where mixes of blocked mercaptosilanes are used for their various blocking or leaving functionalities. Moreover, it is understood that the partial hydrolyzates of these blocked mercaptosilanes (i.e., blocked mercaptosiloxanes) may also be encompassed by the blocked mercaptosilanes herein, in that these partial hydrolyzates will be a side product of most methods of manufacture of the blocked mercaptosilane or can occur upon storage of the blocked mercaptosilane, especially in humid conditions.

The silane, if liquid, may be loaded on a carrier, such as a porous polymer, carbon black or silica so that it is in solid form for delivery to the rubber. In a preferred mode, the carrier would be part of the inorganic filler to be used in the rubber.

Manufacture of Silanes

The methods of preparation for blocked mercaptosilanes may be found in copending PCT/US98/17391; U.S. Pat. No. 3,692,812; Gornowicz, G., "Preparation of Silylalkanethiols", *J. Org. Chem.,* Vol. 33, No. 7, July, 1968; Vorkonov, M. G., et al., "Trialkoxysilylalkanethiols and Bis(trialkoxysilylakyl)sulfides", *Izvestiya Akademii Nauk SSSR,* Seriya Khimicheskeya, No. 8, pp. 1849–51, August 1977, which are incorporated herein by reference.

Utility

The blocked mercaptosilanes described herein are useful as coupling agents for organic polymers (i.e., rubbers) and inorganic fillers. The blocked mercaptosilanes are unique in that the high efficiency of the mercapto group can be utilized without the detrimental side effects typically associated with the use of mercaptosilanes, such as high processing viscosity, less than desirable filler dispersion, premature curing (scorch), and odor. These benefits are accomplished because the mercaptan group initially is non-reactive because of the blocking group. The blocking group substantially prevents the silane from coupling to the organic polymer during the compounding of the rubber. Generally, only the reaction of the silane —SiX$_3$ group with the filler can occur at this stage of the compounding process. Thus, substantial coupling of the filler to the polymer is precluded during mixing, thereby minimizing the undesirable premature curing (scorch) and the associated undesirable increase in viscosity. One can achieve better cured filled rubber properties, such as a balance of high modulus and abrasion resistance, because of the avoidance of premature curing.

In use, one or more of the blocked mercaptosilanes are mixed with the organic polymer before, during or after the compounding of the filler into the organic polymer. It is preferred to add the silanes before or during the compounding of the filler into the organic polymer, because these silanes facilitate and improve the dispersion of the filler. The total amount of silane present in the resulting combination should be about 0.05 to about 25 parts by weight per hundred parts by weight of organic polymer (phr); more preferably 1 to 10 phr. Fillers can be used in quantities ranging from about 5 to about 100 phr, more preferably from 25 to 80 phr.

When reaction of the mixture to couple the filler to the polymer is desired, a deblocking agent is added to the mixture to deblock the blocked mercaptosilane. The deblocking agent may be added at quantities ranging from about 0.1 to about 5 phr; more preferably in the range of from 0.5 to 3 phr. The deblocking agent may be a nucleophile containing a hydrogen atom sufficiently labile such that hydrogen atom could be transferred to the site of the original blocking group to form the mercaptosilane. Thus, with a blocking group acceptor molecule, an exchange of hydrogen from the nucleophile would occur with the blocking group of the blocked mercaptosilane to form the mercaptosilane and the corresponding derivative of the nucleophile containing the original blocking group. This transfer of the blocking group from the silane to the nucleophile could be driven, for example, by a greater thermodynamic stability of the products (mercaptosilane and nucleophile containing the blocking group) relative to the initial reactants (blocked mercaptosilane and nucleophile). For example, carboxyl blocking groups deblocked by amines would yield amides, sulfonyl blocking groups deblocked by amines would yield sulfonamides, sulfinyl blocking groups deblocked by amines would yield sulfinamides, phosphonyl blocking groups deblocked by amines would yield phosphonamides, phosphinyl blocking groups deblocked by amines would yield phosphinamides. What is important is that regardless of the blocking group initially present on the blocked mercaptosilane and regardless of the deblocking agent used, the initially substantially inactive (from the standpoint of coupling to the organic polymer) blocked mercaptosilane is substantially converted at the desired point in the rubber compounding procedure to the active mercaptosilane. It is noted that partial amounts of the nucleophile may be used (i.e., a stoichiometric deficiency), or even weak nucleophile, if one were to only deblock part of the blocked mercaptosilane to control the degree of vulcanization of a specific formulation.

The deblocking agent could be added in the curative package or, alternatively, at any other stage in the compounding process as a single component. Classes of compounds which would act as deblocking agents, but not normally effective as cure accelerators, allowing for selection between the two, are oxides, hydroxides, carbonates, bicarbonates, alkoxides, phenoxides, sulfanamide salts, acetyl acetonates, carbon anions deribved from high acidity C—N bonds, malonic acid esters, cyclopentadienes, phenols, sulfonamides, nitrites, fluorenes, tetra-alkyl ammonium salts, and tetra-alkyl phosphonium salts.

The rubber composition need not be, but preferably is, essentially free of functionalized siloxanes, especially those of the type disclosed in Australian Patent AU-A-10082/97, which is incorporated herein by reference. Most preferably the rubber composition is free of functionalized siloxanes.

In practice, sulfur vulcanized rubber products typically are prepared by thermomechanically mixing rubber and various ingredients in a sequentially step-wise manner followed by shaping and curing the compounded rubber to form a vulcanized product. First, for the aforesaid mixing of the rubber and various ingredients, typically exclusive of sulfur and sulfur vulcanization accelerators (collectively "curing agents"), the rubber(s) and various rubber compounding ingredients typically are blended in at least one, and often (in the case of silica filled low rolling resistance tires) two or more, preparatory thermomechanical mixing stage(s) in suitable mixers. Such preparatory mixing is referred to as nonproductive mixing or non-productive mixing steps or stages. Such preparatory mixing usually is conducted at temperatures up to 140° C. to 200° C. and often up to 150° C. to 180° C. Subsequent to such preparatory mix stages, in a final mixing stage, sometimes referred to as a productive mix stage, deblocking agent (in the case of this invention), curing agents, and possibly one or more additional ingredients, are mixed with the rubber compound or composition, typically at a temperature in a range of 50° C. to 130° C., which is a lower temperature than the temperatures utilized in the preparatory mix stages to prevent or retard premature curing of the sulfur curable rubber, which is sometimes referred to as scorching of the rubber composition. The rubber mixture, sometimes referred to as a rubber compound or composition, typically is allowed to cool, sometimes after or during a process intermediate mill mixing, between the aforesaid various mixing steps, for example, to a temperature of about 50° C. or lower. When it is desired to mold and to cure the rubber, the rubber is placed into the appropriate mold at about at least 130° C. and up to about 200° C., which will cause the vulcanization of the rubber by the mercapto groups on the mercaptosilane and any other free sulfur sources in the rubber mixture.

By thermomechanical mixing, it is meant that the rubber compound, or composition of rubber and rubber compounding ingredients, is mixed in a rubber mixture under high shear conditions where it autogeneously heats up as a result of the mixing primarily due to shear and associated friction within the rubber mixture in the rubber mixer. Several chemical reactions may occur at various steps in the mixing and curing processes.

The first reaction is a relatively fast reaction and is considered herein to take place between the filler and the $SiX_3$ group of the blocked mercaptosilane. Such reaction may occur at a relatively low temperature such as, for example, at about 120° C. The second and third reactions are considered herein to be the deblocking of the mercaptosilane and the reaction which takes place between the sulfuric part of the organosilane (after deblocking), and the sulfur vulcanizable rubber at a higher temperature; for example, above about 140° C.

Another sulfur source may be used, for example, in the form of elemental sulfur as $S_8$. A sulfur donor is considered herein as a sulfur containing compound which makes sulfur available for vulcanization at a temperature of 140° C. to 190° C. such sulfur donors may be, for example, although are not limited to, polysulfide vulcanization accelerators and organosilane polysulfides with at least two connecting sulfur atoms in its polysulfide bridge. The amount of free sulfur source addition to the mixture can be controlled or manipulated as a matter of choice relatively independently from the addition of the aforesaid blocked mercaptosilane. Thus, for example, the independent addition of a sulfur source may be manipulated by the amount of addition thereof and by sequence of addition relative to addition of other ingredients to the rubber mixture.

Addition of an alkyl silane to the coupling agent system (blocked mercaptosilane plus additional free sulfur source and/or vulcanization accelerator) typically in a mole ratio of alkyl silane to blocked mercaptosilane in a range of $\frac{1}{50}$ to $\frac{1}{2}$ promotes an even better control of rubber composition processing and aging.

A rubber composition is prepared by a process which comprises the sequential steps of:
(A) thermomechanically mixing, in at least one preparatory mixing step, to a temperature of 140° C. to 200° C., alternatively to 140° C. to 190° C., for a total mixing time of 2 to 20, alternatively 4 to 15, minutes for such mixing step(s)
(i) 100 parts by weight of at least one sulfur vulcanizable rubber selected from conjugated diene homopolymers and copolymers, and copolymers of at least one conjugated diene and aromatic vinyl compound, (ii) 5 to 100, preferably 25 to 80, phr (parts per hundred rubber) of particulate filler, wherein preferably the filler contains 1 to 85 weight percent carbon black (iii) 0.05 to 20 parts by weight filler of at least one blocked mercaptosilane;
(B) subsequently blending therewith, in a final thermomechanical mixing step at a temperature to 50° C. to 130° C. for a time sufficient to blend the rubber, preferably between 1 to 30 minutes, more preferably 1 to 3 minutes, at least one deblocking agent at about 0.05 to 20 parts by weight of the filler and a curing agent at 0 to 5 phr; and optionally
(C) curing said mixture at a temperature of 130 to 200° C. for about 5 to 60 minutes.

The process may also comprise the additional steps of preparing an assembly of a tire or sulfur vulcanizable rubber with a tread comprised of the rubber composition prepared according to this invention and vulcanizing the assembly at a temperature in a range of 130° C. to 200° C.

Suitable organic polymers and fillers are well known in the art and are described in numerous texts, of which two examples include *The Vanderbilt Rubber Handbook;* R. F. Ohm, ed.; R. T. Vanderbilt Company, Inc., Norwalk, Conn.; 1990 and *Manual For The Rubber Industry;* T. Kempermann, S. Koch, J. Sumner, eds.; Bayer A G, Leverkusen, Germany; 1993. Representative examples of suitable polymers include solution styrene-butadiene rubber (SSBR), styrene-butadiene rubber (SBR), natural rubber (NR), polybutadiene (BR), ethylene-propylene co- and terpolymers (EP, EPDM), and acrylonitrile-butadiene rubber (NBR). The rubber composition is comprised of at least one diene-based elastomer, or rubber. Suitable conjugated dienes are isoprene and 1,3-butadiene and suitable vinyl aromatic compounds are styrene and alpha methyl styrene. Thus, the rubber is a sulfur curable rubber. Such diene based elastomer, or rubber, may be selected, for example, from at least one of cis-1,4-polyisoprene rubber (natural and/or synthetic), and preferably natural rubber), emulsion polymerization prepared styrene/butadiene copolymer rubber, organic solution polymerization prepared styrene/butadiene rubber, 3,4-polyisoprene rubber, isoprene/butadiene rubber, styrene/isoprene/butadiene terpolymer rubber, cis-1,4-polybutadiene, medium vinyl polybutadiene rubber (35–50 percent vinyl), high vinyl polybutadiene rubber (50–75 percent vinyl), styrene/isoprene copolymers, emulsion polymerization prepared styrene/butadiene/acrylonitrile terpolymer rubber and butadiene/acrylonitrile copolymer rubber. An emulsion polymerization derived styrene/butadiene (E-SBR) might be used having a relatively conventional styrene content of 20 to 28 percent bound styrene or, for some applications, an E-SBR having a medium to relatively high bound styrene content, namely, a bound styrene content of 30 to 45 percent. Emulsion polymerization prepared styrene/butadiene/acrylonitrile terpolymer rubbers containing 2 to 40 weight percent bound acrylonitrile in the terpolymer are also contemplated as diene based rubbers for use in this invention.

The solution polymerization prepared SBR (S-SBR) typically has a bound styrene content in a range of 5 to 50, preferably 9 to 36, percent. Polybutadiene elastomer may he conveniently characterized, for example, by having at least a 90 weight percent cis-1,4-content.

Representative examples of suitable filler materials include include metal oxides, such as silica (pyrogenic and precipitated), titanium dioxide, aluminosilicate and alumina, siliceous materials including clays and talc, and carbon black. Particulate, precipitated silica is also sometimes used for such purpose, particularly when the silica is used in connection with a silane. In some cases, a combination of silica and carbon black is utilized for reinforcing fillers for various rubber products, including treads for tires. Alumina can be used either alone or in combination with silica. The term "alumina" can be described herein as aluminum oxide, or $Al_2O_3$. The fillers may be hydrated or in anhydrous form.

Use of alumina in rubber compositions can be shown, for example, in U.S. Pat. No. 5,116,886 and EP 631 982.

The blocked mercaptosilane may be premixed, or pre-reacted, with the filler particles or added to the rubber mix during the rubber and filler processing, or mixing stage. If the silane and filler are added separately to the rubber mix during the rubber and filler mixing, or processing stage, it is considered that the blocked mercaptosilane then combines in situ with the filler.

The vulcanized rubber composition should contain a sufficient amount of filler to contribute a reasonably high modulus and high resistance to tear. The combined weight of the filler may be as low as about 5 to 100 phr, but is more preferably from 25 to 85 phr.

Precipitated silicas are preferred as the filler. The silica may be characterized by having a BET surface area, as measured using nitrogen gas, preferably in the range of 40 to 600, and more usually in a range of 50 to 300 $m^2$/g. The BET method of measuring surface area is described in the *Journal of the American Chemical Society*, Volume 60, page 304 (1930). The silica typically may also be characterized by having a dibutylphthalate (DBP) absorption value in a range of 100 to 350, and more usually 150 to 300. Further, the silica, as well as the aforesaid alumina and aluminosilicate, may be expected to have a CTAB surface area in a range of 100 to 220. The CTAB surface area is the external surface area as evaluated by cetyl trimethylammonium bromide with a pH of 9. The method is described in ASTM D 3849.

Mercury porosity surface area is the specific surface area determined by mercury porosimetry. For such technique, mercury is penetrated into the pores of the sample after a thermal treatment to remove volatiles. Set up conditions may be suitably described as using a 100 mg sample; removing volatiles during 2 hours at 105° C. and ambient atmospheric pressure; ambient to 2000 bars pressure measuring range. Such evaluation may be performed according to the method described in Winslow, Shapiro in ASTM bulletin, p.39 (1959) or according to DIN 66133. For such an evaluation, a CARLO-ERBA Porosimeter 2000 might be used. The average mercury porosity specific surface area for the silica should be in a range of 100 to 300 $m^2$/g.

A suitable pore size distribution for the silica, alumina and aluminosilicate according to such mercury porosity evaluation is considered herein to be: five percent or less of its pores have a diameter of less than about 10 nm; 60 to 90 percent of its pores have a diameter of 10 to 100 nm; 10 to 30 percent of its pores have a diameter at 100 to 1,000 nm; and 5 to 20 percent of its pores have a diameter of greater than about 1,000 nm.

The silica might be expected to have an average ultimate particle size, for example, in the range of 0.01 to 0.05 $\mu$m as determined by the electron microscope, although the silica particles may be even smaller, or possibly larger, in size. Various commercially available silicas may be considered for use in this invention such as, from PPG Industries under the HI-SIL trademark with designations HI-SIL 210, 243, etc.; silicas available from Rhone-Poulenc, with, for example, designation of ZEOSIL 1165MP; silicas available from Degussa with, for example, designations VN2 and VN3, etc. and silicas commercially available from Huber having, for example, a designation of HUBERSIL 8745.

Where it is desired for the rubber composition, which contains both a siliceous filler such as silica, alumina and/or aluminosilicates and also carbon black reinforcing pigments, to be primarily reinforced with silica as the reinforcing pigment, it is often preferable that the weight ratio of such siliceous fillers to carbon black is at least 3/1 and preferably at least 10/1 and, thus, in a range of 3/1 to 30/1. The filler may be comprised of 15 to 95 weight percent precipitated silica, alumina and/or aluminosilicate and, correspondingly, 5 to 85 weight percent carbon black, wherein the said carbon black has a CTAB value in a range of 80 to 150. Alternatively, the filler can be comprised of 60 to 95 weight percent of said silica, alumina and/or aluminosilicate and, correspondingly, 40 to 5 weight percent carbon black. The siliceous filler and carbon black may be pre-blended or blended together in the manufacture of the vulcanized rubber.

The rubber composition may be compounded by methods known in the rubber compounding art, such as mixing the various sulfur-vulcanizable constituent rubbers with various commonly used additive materials such as, for example, curing aids, such as sulfur, activators, retarders and accelerators, processing additives, such as oils, resins including tackifying resins, silicas, plasticizers, fillers, pigments, fatty acid, zinc oxide, waxes, antioxidants and antiozonants, peptizing agents, and reinforcing materials such as, for example, carbon black. Depending on the intended use of the sulfur vulcanizable and sulfur vulcanized material (rubbers), the additives mentioned above are selected and commonly used in conventional amounts.

The vulcanization may be conducted in the presence of an additional sulfur vulcanizing agent. Examples of suitable sulfur vulcanizing agents include, for example elemental sulfur (free sulfur) or sulfur donating vulcanizing agents, for example, an amino disulfide, polymeric polysulfide or sulfur olefin adducts which are conventionally added in the final, productive, rubber composition mixing step. The sulfur vulcanizing agents (which are common in the art) are used, or added in the productive mixing stage, in an amount ranging from 0.4 to 3 phr, or even, in some circumstances, up to about 8 phr, with a range of from 1.5 to 2.5 phr, sometimes from 2 to 2.5 phr, being preferred.

Vulcanization accelerators may be used herein. It is appreciated that they may be, for example, of the type such as, for example, benzothiazole, alkyl thiuram disulfide, guanidine derivatives and thiocarbamates. Vulcanization accelerators may be primary or secondary accelerators and individual accelerators may function as either primary or secondary accelerators. Representative of such accelerators are, for example, but not limited to, mercapto benzothiazole, tetramethyl thiuram disulfide, benzothiazole disulfide, diphenylguanidine, zinc dithiocarbamate, alkylphenoldisulfide, zinc butyl xanthate, N-dicyclohexyl-2-benzothiazolesulfenamide, N-cyclohexyl-2-benzothiazolesulfenamide, N-oxydiethylenebenzothiazole-2-sulfenamide, N,N-diphenylthiourea, dithiocarbamylsulfenamide, N,N-diisopropylbenzothiozole-2-sulfenamide, zinc-2-mercaptotoluimidazole, dithiobis(N-methyl piperazine), dithiobis(N-beta-hydroxy ethyl piperazine) and dithiobis(dibenzyl amine). Other additional sulfur donors, may be, for example, thiuram and morpholine derivatives. Representative of such donors are, for example, but not limited to, dimorpholine disulfide, dimorpholine tetrasulfide, tetramethyl thiuram tetrasulfide, benzothiazyl-2,N-dithiomorpholide, thioplasts, dipentamethylenethiuram hexasulfide, and disulfidecaprolactam.

Accelerators are used to control the time and/or temperature required for vulcanization and to improve the properties of the vulcanizate. In one embodiment, a single accelerator system may be used, i.e., a primary accelerator. Conventionally and preferably, a primary accelerator(s) is used in total amounts ranging from 0.5 to 4, preferably 0.8 to 1.5, phr. Combinations of a primary and a secondary accelerator might be used with the secondary accelerator being used in smaller amounts (of 0.05 to 3 phr) in order to activate and to improve the properties of the vulcanizate. Delayed action accelerators may be used. Vulcanization retarders might also be used. Suitable types of accelerators are amines, disulfides, guanidines, thioureas, thiazoles, thiurams, sulfenamides, dithiocarbamates and xanthates, but the type may be influenced if the accelerant is also a deblocker. Examples of primary accelerators used in the art include N-cyclohexyl-2-benzothiazyl sulfenamide (CBS); N-t-butyl-2-benzothiazyl sulfenamide (TBBS); benzothiazyl-2-sulphene morpholide (MBS); N-dicyclohexyl-2-benzothiazyl sulfenamide (DCBS); tetramethylthiuram monosulfide (TMTM); tetramethylthiuram disulfide (TMTD); tetramethylthiuram hexasulfide; N,N-diphenylurea; and morpholinethiobenzothiazole. If a second accelerator is used, the secondary accelerator is preferably a guanidine, dithiocarbamate or thiuram compound. Examples of secondary accelerators commonly used in the art include diphenylguanidine (DPG); tetramethylthiuram hexasulfide; mercaptobenzothiazole (MBT); mercaptobenzothiazole disulfide (MBTS); the zinc salt of mercaptobenzothiazole (ZMBT); Zinc dibutyldithiocarbamate; Zinc diethyldithiocarbamate; Zinc dimethyldithiocarbamate; Zinc dibenzyldithiocarbamate; Zinc ethylphenyldithiocarbamate; Nickel dibutyldithiocarbamate; Copper dimethyldithiocarbamate; piperidinium pentamethylene dithiocarbamate; thiocarbanilide; 1,3-diethylthiourea; 1,3-dibutylthiourea; di(pentamethylene)thiuram hexasulfide; and morpholinethiobenzothiazole. Numerous specific examples of guanidines, amines, and imines well known in the art, which are useful as components in curatives for rubber, are cited in *Rubber Chemicals;* J. Van Alphen; Plastics and Rubber Research Institute TNO, Delft, Holland; 1973.

In elastomer formulations of the present invention, it is important to consider an additional factor in the choice of the accelerator system. This factor is related to the deblocking action of the accelerator on the blocked mercaptosilane. Deblocking of the blocked mercaptosilane occurs by the catalytic or chemical action of a component added to the elastomer at a point where deblocking is desired. Amines or related basic substances are particularly suitable in this regard. Most of the aforementioned accelerators are amine based, but their basicity may be reduced because the nitrogen atom is bound to a sulfur atom, carbonyl, or thiocarbonyl. This influences the type of accelerator package ideally suited for elastomer compositions of the present invention. Thus, a preferred method of operation would be to use such amines as both deblocking agent and accelerator.

Among the accelerators of demonstrated suitability for use with blocked mercaptosilanes are diphenylguanidine (DPG) and tetramethylthiuram monosulfide (TMTM). The TMTM is preferred. It is believed that the family of such compounds, i.e., $R_2NC(=S)-S_n-C(=S)NR_2$ wherein n=1 to 4, R is an akyl group of 1 to 4 carbon atoms, would be preferred.

Free amines, or closely related chemical compounds, such as imines, anilines, and nitrogen-containing heterocycles are expected to deblock and thereby activate the blocked mercaptosilanes much more readily, rapidly, and/or completely than many of the aforementioned accelerators on the basis of their stronger basicity. Suitable amine accelerators would be secondary or tertiary amines containing substantial carbon content so that they contain sufficient hydrophobicity in their structure to offset the hydrophilicity of the basic amine group, so that dispersion into the rubber matrix is promoted. All such compounds should have boiling points of at least 140C and preferably >200C. This includes secondary or tertiary amines with enough carbon content to be miscible in the rubber mixture, generally about a molar ratio of C:N of at least 6:1. Alternatively, the amine may be a heterocyclic amine of the following classes: quinoline, imidazoline, imidazolidone, hydantoin, hydralazine, pyrazole, pyrazine, purine, pyrimidine, pyrrole, indole, oxazole, thiazole, benzimidazole, benzoxazole, benzothiazole, triazole, benzotriazole, tetrazole, aniline, phenylene diamine, and imine. Factors in considering the accelerators of the free amine type would, of course, be factors such as toxicity, physical state (i.e. liquid or solid), volatility, its ability to disperse into the formulation, etc.

Most suitably, one can use mixtures of the vulcanization accelerators, which are used to deblock the silane with the aforementioned deblocking agents to control the rate and degree of rubber cure as to to deblocking and crosslinking of the silane. Each rubber mixture will have its own optimal blend which may be determined by simple experimentation.

Typical amounts of tackifier resins, if used, comprise 0.5 to 10 phr, usually 1 to 5 phr. Typical amounts of processing aids comprise 1 to 50 phr. Such processing aids can include, for example, aromatic, napthenic, and/or paraffinic processing oils. Typical amounts of antioxidants comprise 1 to 5 phr. Representative antioxidants may be, for example, diphenyl-p-phenylenediamine and others, such as, for example, those disclosed in the *Vanderbilt Rubber Handbook* (1978), pages 344–346. Typical amounts of antiozonants, comprise 1 to 5 phr. Typical amounts of fatty acids, if used, which can include stearic acid, comprise 0.5 to 3 phr. Typical amounts of zinc oxide comprise 2 to 5 phr. Typical amounts of waxes comprise 1 to 5 phr. Often microcrystalline waxes are used. Typical amounts of peptizers comprise 0.1 to 1 phr. Typical peptizers may be, for example, pentachlorothiophenol and dibenzamidodiphenyl disulfide.

The rubber composition of this invention can be used for various purposes. For example, it can be used for various tire compounds. Such tires can be built, shaped, molded and cured by various methods which are known and will be readily apparent to those having skill in such art.

All references cited herein are incorporated herein as they are relevant to the present invention.

EXAMPLES

The invention may be better understood by reference to the following examples in which the amounts of reactants are parts per hundred of rubber unless otherwise indicated.

The following tests were conducted with the following methods (in all examples): Mooney Scorch @135° C. (ASTM Procedure D1646); Mooney Viscosity @100° C. (ASTM Procedure D1646); Oscillating Disc Rheometer (ODR) @149° C., 1° arc, (ASTM Procedure D2084); Physical Properties, cured t90 @149° C. (ASTM Procedures D412 and D224) (G' and G" in dynes/cm$^2$); DIN Abrasion, mm$^3$ (DIN Procedure 53516); and Heat Build (ASTM Procedure D623).

Formulation: 75 Solflex 1216 sSBR, 25 Budene 1207 BR, 80 Zeosil 1165MP silica, 32.5 Sundex 3125 process oil, 2.5 Kadox 720C zinc oxide, 1.0 Industrene R stearic acid, 2.0 Santoflex 13 antiozonant, 1.5 M4067 microwax, 3.0 N330 carbon black, 1.4 Rubbermakers sulfur 104, 1.7 CBS, 2.0 DPG. The silanes are SILQUEST A-1289 polysulfide bissilane from Witco Corp. (comparative) and OTPTE is 3-octylthioacetylpropyl triethoxysilane ($C_8H_{17}C(=O)SC_3H_6Si(OC_2H_5)_3$.

Example 1
Comparison of TMTM and DPG

| Silane | A1289 | A1289* | OTPTE | OTPTE* |
|---|---|---|---|---|
| Loading | 7 | 7 | 9.7 | 9.7 |
| Mooney Viscosity @ 100° C. |  |  |  |  |
| ML1 + 4 | 73 | 73 | 55 | 55 |
| Mooney Scorch @ 135° C. |  |  |  |  |
| MS1 + , $t_3$, minutes | 6.6 | 6.8 | 10.4 | 9.4 |
| MS1 + , $t_{18}$, minutes | 9.7 | 8.5 | 11.7 | 11.1 |
| ODR @ 149° C., 1° arc, 30 minute timer |  |  |  |  |
| $M_L$, in.-lb. | 8.3 | 8.5 | 5.9 | 5.5 |
| $M_H$, in.-lb. | 27.7 | 30.4 | 24.6 | 33.0 |
| $t_{s1}$, minutes | 5.0 | 4.3 | 5.6 | 5.6 |
| t90, minutes | 17.5 | 10.3 | 11.3 | 12.5 |
| Physical Properties, cured t90 @ 149° C. |  |  |  |  |
| Hardness, Shore A | 58 | 58 | 53 | 62 |
| Elongation, % | 420 | 390 | 600 | 380 |
| 100% Modulus, psi. | 300 | 320 | 200 | 420 |
| 200% Modulus, psi. | 900 | 1020 | 490 | 1160 |
| 300% Modulus, psi. | 1970 | 2200 | 1100 | 2110 |
| Tensile, psi. | 3330 | 3320 | 3240 | 2780 |
| DIN Abrasion, $mm^3$ | 97 | 73 | 99 | 66 |
| Heat Build-up @ 212° F., 17.5% compression, 143 psi. static load |  |  |  |  |
| Delta T, F ° | 25 | 19 | 22 | 13 |
| Permanent set, % | 10.7 | 4.5 | 5.0 | 1.4 |
| Dynamic Properties @ 0.15% strain, 10 HZ, torsion mode |  |  |  |  |
| G' @ 0° C., × $10^7$ | 6.67 | 6.49 | 4.80 | 7.38 |
| G' @ 60° C., × $10^7$ | 2.88 | 2.80 | 2.44 | 3.44 |
| G" @ 0° C., × $10^7$ | 1.46 | 1.43 | 0.98 | 1.39 |
| G" @ 60° C., × $10^6$ | 2.82 | 2.33 | 2.14 | 2.14 |
| Tan delta @ 0° C. | 0.2193 | 0.2203 | 0.205 | 0.1882 |
| Tan delta @ 60° C. | 0.0979 | 0.0832 | 0.088 | 0.0620 |
| Ratio, 0° C./60° C. | 2.24 | 2.64 | 2.33 | 3.04 |

*TMTM substituted for DPG

The data shows that changing the accelerant with a non-blocked sulfur silane (A-1289) has an insubstantial effect, whereas changing the accelerant with regard to the blocked mercaptosilane provides a dramatic improvement in the physical properties of the rubber, i.e., an increase in 300% modulus and a major improvement in the tan delta ratio.

What is claimed is:

1. A process for the manufacture of a filled rubber comprising:

a. mixing an rubber, a blocked mercaptosilane and inorganic filler;

b. mixing into the mixture of step (a) a deblocking agent of the formula $R_2NC(=S)-S_n-C(=S)NR_2$ wherein n=1 to 4, R is an akyl group of 1 to 4 carbon atoms; and c. allowing the mixture to cure.

2. A process according to claim 1 wherein mercaptosilane is selected from the group consisting of:

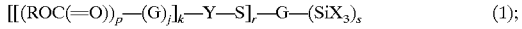

and

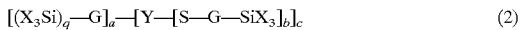

wherein

Y is a polyvalent species $(Q)_zA(=E)$, each wherein the atom (A) attached to the unsaturated heteroatom (E) is attached to the sulfur, which in turn is linked via a group G to the silicon atom;

each R is chosen independently from hydrogen, straight, cyclic or branched alkyl that may or may not contain unsaturation, alkenyl groups, aryl groups, and aralkyl groups, with each R containing from 1 to 18 carbon atoms;

each G is independently a monovalent or polyvalent group derived by substitution of alkyl, alkenyl, aryl or aralkyl wherein G can contain from 1 to 18 carbon atoms, with the proviso that G is not such that the silane would contain an α,β-unsaturated carbonyl including a carbon—carbon double bond next to the thiocarbonyl group, and if G is univalent, G can be a hydrogen atom;

X is independently selected from the group consisting of —Cl, —Br, RO—, RC(=O)O—, $R_2C=NO-$, —$R_2NO-$, $R_2N-$, —R and —$(OSiR_2)_t(OsiR_3)$, wherein each R and G is as above and at least one X is not —R;

Q is oxygen, sulfur or (—NR—);

A is carbon, sulfur, phosphorus, or sulfonyl;

E is oxygen, sulfur or NR;

p is 0 to 5; r is 1 to 3; z is 0 to 2; q is 0 to 6; a is 0 to 7; b is 1 to 3; j is 0 to 1, but it may be 0 only if p is 1, c is 1 to 6, t is 0 to 5; s is 1 to 3; k is 1 to 2, with the provisos that (A) if A is carbon, sulfur or sulfonyl, then (i) a+b=2 and (ii) k=1; (B) if A is phosphorus, then a+b=3 unless both (i) c>1 and (ii) b=1, in which case a=c+1; and (C) if A is phosphorus, then k is 2.

3. A process according to claim 2 wherein Y is —C(=O)—.

4. A process according to claim 3 wherein each X is RO—, the silane is of formula (1), r=1 and s=1.

5. A process according to claim 2 wherein the deblocking agent is tetramethylthiuram monosulfide.

* * * * *